United States Patent [19]

Cameron

[11] Patent Number: 4,924,876

[45] Date of Patent: May 15, 1990

[54] NASAL BREATH MONITOR

[76] Inventor: Peter Cameron, P.O. Box 404, Upton, N.Y. 11973

[21] Appl. No.: 116,697

[22] Filed: Nov. 4, 1987

[51] Int. Cl.$^5$ .............................................. A61B 5/08
[52] U.S. Cl. ................................. 128/725; 128/200.24
[58] Field of Search .................. 128/725, 720, 200.24, 128/724; 364/413.03

[56] References Cited

U.S. PATENT DOCUMENTS

| 3,991,304 | 11/1976 | Hillsman | 128/725 |
| 4,519,399 | 5/1985 | Hori | 128/725 X |
| 4,727,886 | 3/1988 | Conrardy et al. | 128/725 |

FOREIGN PATENT DOCUMENTS 2575917  7/1986  France .............................. 128/724

OTHER PUBLICATIONS

Graf; Dictionary of Electronics, 1973, p. 483.

Primary Examiner—William E. Wayner

[57] ABSTRACT

A nasal breath monitor, which uses separate sensors for each nostril to detect the flow of the breath, electronic circuitry to amplify and enhance the detected signal, and stereo headphones to bring this information to the ears.

10 Claims, 2 Drawing Sheets

NASAL BREATH MONITOR

BACKGROUND OF THE INVENTION

1. Field of the Invention

The invention relates generally to a device for monitoring the flow of the nasal breath, and for making this information immediately available to the user with stereo headphones.

2. Description of the Prior Art

Breath monitors currently in use monitor the flow of breath through the mouth. The problem with these breath monitors is that they are unsuitable for use which is specifically directed towards relaxation and stress reduction, because the breathing techniques which have been found productive for relaxation and stress reduction require that the breath be directed through the nostrils. In addition, it is useful to examine the flow through each nostril seperately, because variations in their relative magnitudes have been shown to be both an indicator and a controller of the ultradian rhythm, a rhythm which is of fundamental importance in the regulation of physiological states in the body and their corresponding correlates in the mind. Finally, none of the breath monitors currently in use provide the user with an immediate output which is representative of the balance and smoothness of the breath. This is a problem because the user is then deprived of the benefit of feedback, which enhances the depth of relaxation and stress reduction. This invention eliminates these problems.

SUMMARY OF THE INVENTION

The invention relates to a device for making the user more aware of the quality of the breath. It comprises seperate sensors for each nostril to detect the flow of the breath, electronic circuitry to amplify and enhance the detected signal, and stereo headphones to bring this information to the ears of the user.

DESCRIPTION OF THE PREFERRED EMBODIMENT

Figure 1:
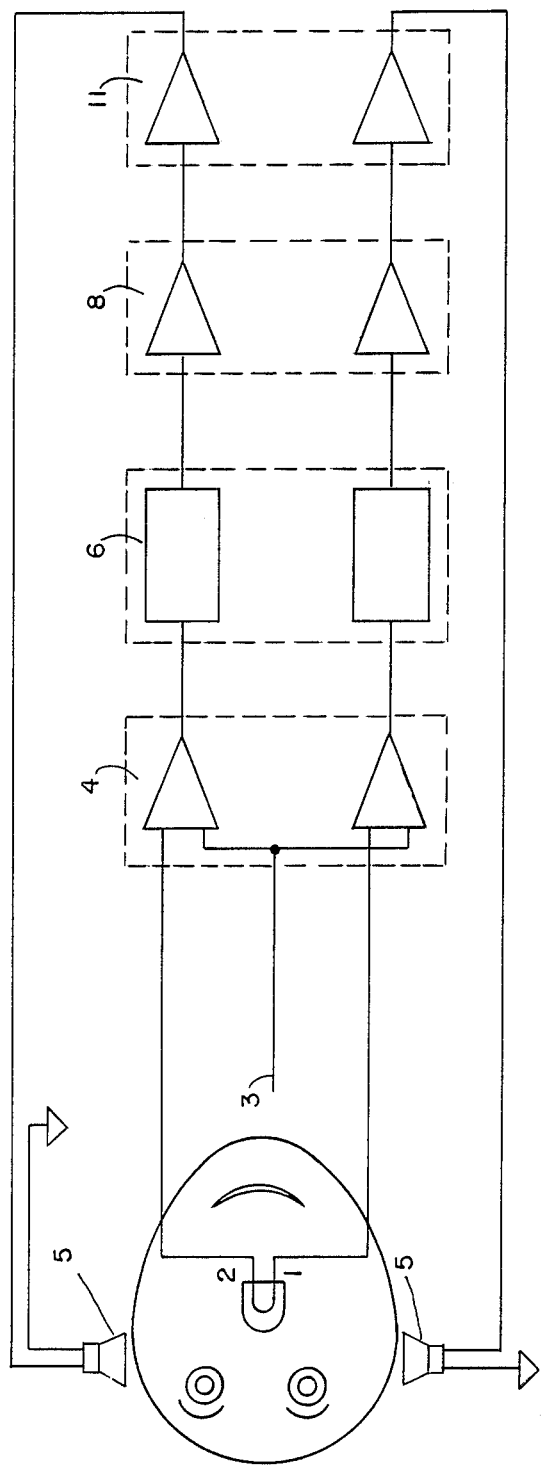
FIGS. 1 and 2 are labelled representation showing a Nasal Breath Monitor, including the sensors, differential amplifiers, compressors, low-pass filters, power amplifiers, and headphones.
Figure 2:
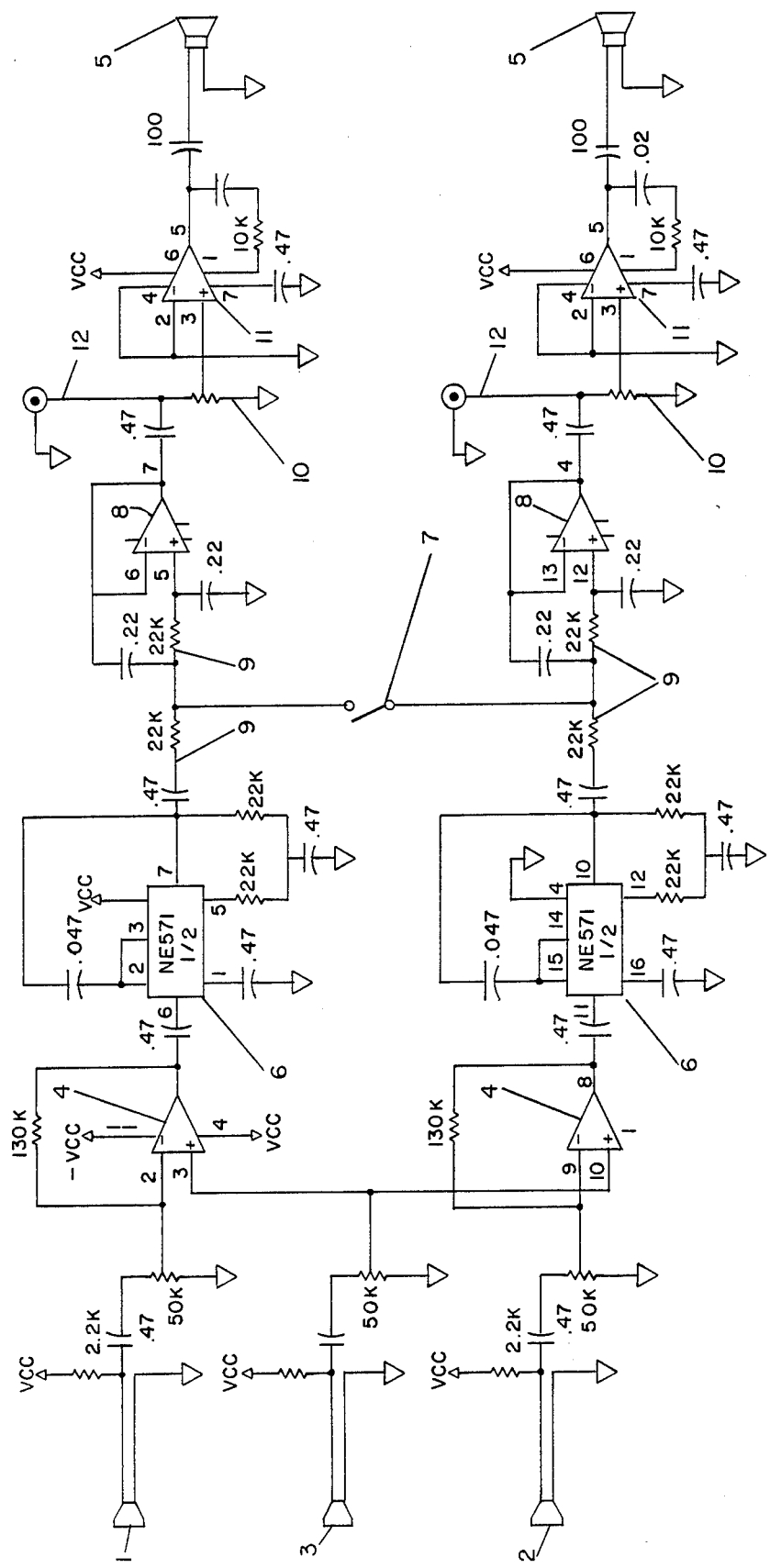

Referring to FIGS. 1 and 2, an embodiment of the Nasal Breath Monitor is shown. The sensors (1,2,3) comprise miniature condensor electret microphones. They contain built in field effect transistor amplifiers. Their output is in the range from 1 to 100 millivolts. In addition to the two microphones 1, 2 for the nostrils, a third microphone 3 is employed as a reference sensor. This permits the use of a differential amplifier 4 in the first stage, reducing ambient noise and eliminating the audio feedback path between the microphones and the headphones 5.

The gain of the differential amplifier is adjusted so that low level mistracking is not a problem in the compressor 6. The compressor is an integrated circuit developed for noise reduction in the telephone system. Its use here is not for noise reduction, but rather to make the quiet sounds louder and the loud sounds quieter, so that the gain can be high enough to hear very gentle breathing without the user being deafened by the explosive turbulence of a sneeze.

A mono/stereo switch 7 is located between the compressor and the low-pass filter 8. The series resistors 9, which are part of the filter's cut-off circuitry, provide a convenient place to isolate this switch, which is useful for setting up the monitor.

The low-pass filter utilizes the remaining two amplifiers from the integrated circuit used for the differential amplifiers. It enhances tonal pleasantness, eliminating annoying high frequency whistling and also eliminating phase noise from the reference sensor, which otherwise becomes a problem when wavelengths are of the order of the seperation distance between the sensors.

Gain is adjusted with the potentiometer 10 between the filter and the power amplifier 11. A preamp output 12 is made available immediately before the potentiometer, to permit the user to adjust volume as desired without affecting the data quality.

BRIEF DESCRIPTION OF OPERATION

Referring to FIG. 2, the outputs of the left nostril sensor(2) and the reference sensor(3) are differentially amplified(4), so that ambient disturbances are cancelled. The dynamic range is greatly increased by signal compression(6), which is followed by low-pass filtering(8). Power amplification(11) is provided to drive the left headphone(5), so that the left ear hears an enhanced sound of the breath in the left nostril. The right channel operates in the same manner.

Referring to FIG. 1, in operation the monitor is first balanced by closing the mono/stereo switch(7). Both ears then hear the same sound, which is a mixture of the sound from both nostrils. Potentiometers(10) are then adjusted until the loudness is comfortable and the balance is such that the sound of the breath seems to be equally loud in both ears. The mono/stereo switch is then switched to stereo.

I claim:

1. A device for monitoring the nasal breath which comprises:
   a. means for seperately sensing the flow of air through the two nostrils; and
   b. means for seperately amplifying the output of said means for sensing the flow of air; and
   c. means for making the said seperate amplified outputs sensible to the user, thereby providing an indication of relative airflow through the two nostrils.

2. A device for monitoring the nasal breath as recited in claim 1, in which said means for sensing the flow of air comprises pressure transducers.

3. A device for monitoring the nasal breath as recited in claim 2, in which said pressure transducers comprise condensor electret microphones.

4. A device for monitoring the nasal breath as recited in claim 1, further comprising an additional means for sensing ambient disturbances, and differential amplifiers to permit cancellation of these ambient disturbances.

5. As device for monitoring the nasal breath as recited in claim 1, in which means for signal compression is used to increase the dynamic range.

6. A device for monitoring the nasal breath as recited in claim 1, in which means for low-pass filtering is used to reduce noise.

7. A device for monitoring the nasal breath as recited in claim 1, in which said means for making the amplified output sensible to the user comprises audio amplifiers and stereo headphones.

8. A device for monitoring the nasal breath as recited in claim 1, in which said means for amplifying the sensed flow of air comprises a differential amplifier, such that the output is proportional to the difference in flow between the two nostrils.

9. A device for monitoring the nasal breath which comprises:
   a. two condensor electret microphones which seperately sense the flow of air through the two nostrils; and
   b. a differential amplifier, which amplifies the difference between the outputs of the two condensor electret microphones; and
   c. means for compression of the differentially amplified signal; and
   d. means for low-pass filtering of the compressed signal; and
   e. means for audio power amplification of the differentially amplified, compressed, and filtered signal; and
   f. headphones to make the said audio power amplified signal audible to the user.

10. A device for monitoring the nasal breath which comprises:
   a. two condensor electret microphones which seperately sense the flow of air through the two nostrils; and
   b. a third condensor electret microphone to provide an ambient reference; and
   c. differential amplifiers, which amplify the difference between the reference microphone and the microphones which sense the flows of air; and
   d. means for compression of the differentially amplified signals; and
   e. means for low-pass filtering of the compressed signals; and
   f. means for audio power amplification of the differentially amplified, compressed, and filtered signals; and
   g. stereo headphones to make the said audio power amplified signals audible to the user.

* * * * *